(12) United States Patent
Bjorkholm

(10) Patent No.: US 8,551,785 B2
(45) Date of Patent: Oct. 8, 2013

(54) DUAL ANGLE RADIATION SCANNING OF OBJECTS

(75) Inventor: Paul Bjorkholm, Newport Beach, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 13/423,860

(22) Filed: Mar. 19, 2012

(65) Prior Publication Data

US 2012/0177175 A1   Jul. 12, 2012

Related U.S. Application Data

(62) Division of application No. 11/485,150, filed on Jul. 12, 2006, now Pat. No. 8,137,976.

(51) Int. Cl.
 *G01N 33/00* (2006.01)
(52) U.S. Cl.
 USPC .......... 436/57; 422/82.05; 422/82.09; 422/91
(58) Field of Classification Search
 USPC ................. 436/57; 422/82.05, 82.09, 91
 See application file for complete search history.

(56) References Cited

U.S. PATENT DOCUMENTS

| | | |
|---|---|---|
| 3,018,374 A | 1/1962 | Pritchett |
| 3,456,113 A | 7/1969 | Keepin |
| 3,636,353 A | 1/1972 | Untermyer |
| 3,924,132 A | 12/1975 | Koslow |
| 4,229,654 A | 10/1980 | Arya et al. |
| 4,251,726 A | 2/1981 | Alvarez |
| 4,345,158 A | 8/1982 | Pfeiler et al. |
| 4,382,208 A | 5/1983 | Meddaugh et al. |
| 4,400,650 A | 8/1983 | Giebeler, Jr. |
| 4,511,799 A | 4/1985 | Bjorkholm |

(Continued)

FOREIGN PATENT DOCUMENTS

| | | |
|---|---|---|
| JP | 6-504838 | 6/1994 |
| JP | 7-505216 | 6/1995 |

(Continued)

OTHER PUBLICATIONS

S. Ogorodnikov, V. Petrunin, "Processing of Interlaced Images in 4-10 MeV Dual Energy Customs system for Material Recognition", Physical Review Special Topics—Accelerators and Beams, 2002, vol. 5, The American Physical Society, College Park, MD.

(Continued)

*Primary Examiner* — Sam P Siefke
(74) *Attorney, Agent, or Firm* — Cozen O'Connor; Brandon N. Sklar

(57) ABSTRACT

In one example, a method of examining contents of an object is disclosed comprising scanning an object by first and second radiation beams at least first and second angles, detecting radiation at the first and second angles, and determining whether the object at least potentially comprises high atomic number material, which may be nuclear material or shielding material, based, at least in part, on the detected radiation. In one example, the detected radiation at both angles must be indicative of a region of high atomic number material by the presence of corresponding high density regions, in order for it to be concluded that high atomic number material that may be nuclear material may be present. The determination may be further based on the size of a high density region in one of the images. Systems are also disclosed.

31 Claims, 10 Drawing Sheets

(56) References Cited

U.S. PATENT DOCUMENTS

| | | | |
|---|---|---|---|
| 4,540,882 | A | 9/1985 | Vinegar et al. |
| 4,671,256 | A | 6/1987 | Lemelson |
| 5,044,002 | A | 8/1991 | Stein |
| 5,065,418 | A | 11/1991 | Bermbach et al. |
| 5,098,640 | A | 3/1992 | Gozani et al. |
| 5,319,547 | A | 6/1994 | Krug et al. |
| 5,410,156 | A | 4/1995 | Miller |
| 5,490,218 | A | 2/1996 | Krug et al. |
| 5,495,106 | A | 2/1996 | Mastny |
| 5,524,133 | A | 6/1996 | Neale et al. |
| 5,557,108 | A | 9/1996 | Tümer |
| 5,600,303 | A | 2/1997 | Husseiny et al. |
| 5,600,700 | A | 2/1997 | Krug et al. |
| 5,611,502 | A | 3/1997 | Edlin et al. |
| 5,682,411 | A | 10/1997 | Rushbrooke et al. |
| 5,692,028 | A | 11/1997 | Geus et al. |
| 5,696,806 | A | 12/1997 | Grodzins et al. |
| 5,729,582 | A | 3/1998 | Ham et al. |
| 5,838,758 | A | 11/1998 | Krug et al. |
| 5,838,759 | A | 11/1998 | Armistead |
| 5,841,832 | A | 11/1998 | Mazess et al. |
| 5,905,806 | A | 5/1999 | Eberhard et al. |
| 5,917,880 | A | 6/1999 | Bjorkholm |
| 6,018,562 | A | 1/2000 | Willson |
| 6,069,936 | A | 5/2000 | Bjorkholm |
| 6,078,642 | A | 6/2000 | Simanovsky et al. |
| 6,088,423 | A | 7/2000 | Krug et al. |
| 6,151,381 | A | 11/2000 | Grodzins et al. |
| 6,195,444 | B1 | 2/2001 | Simanovsky et al. |
| 6,236,709 | B1 | 5/2001 | Perry et al. |
| 6,301,326 | B2 | 10/2001 | Bjorkholm |
| 6,320,193 | B1 | 11/2001 | Morrison et al. |
| 6,347,132 | B1 | 2/2002 | Annis |
| 6,366,021 | B1 | 4/2002 | Meddaugh et al. |
| 6,411,674 | B1 | 6/2002 | Oikawa |
| 6,418,189 | B1 | 7/2002 | Schafer |
| 6,438,201 | B1 | 8/2002 | Mazess et al. |
| 6,449,334 | B1 | 9/2002 | Mazess et al. |
| 6,567,496 | B1 | 5/2003 | Sychev |
| 6,584,170 | B2 | 6/2003 | Aust et al. |
| 6,816,571 | B2 | 11/2004 | Bijjani et al. |
| 6,936,820 | B2 | 8/2005 | Peoples |
| 6,944,263 | B2 | 9/2005 | Xiao et al. |
| 6,944,264 | B2 * | 9/2005 | Bijjani et al. .............. 378/57 |
| 7,023,957 | B2 | 4/2006 | Bijjani et al. |
| 7,045,788 | B2 | 5/2006 | Iwatschenko-Borho et al. |
| 7,103,137 | B2 | 9/2006 | Seppi et al. |
| 7,130,371 | B2 | 10/2006 | Elyan et al. |
| 7,158,611 | B2 | 1/2007 | Heismann et al. |
| 7,162,005 | B2 | 1/2007 | Bjorkholm |
| 7,162,007 | B2 | 1/2007 | Elyan et al. |
| 7,164,750 | B2 | 1/2007 | Nabors et al. |
| 7,215,737 | B2 | 5/2007 | Li et al. |
| 7,257,188 | B2 * | 8/2007 | Bjorkholm .............. 378/53 |
| 7,274,767 | B2 | 9/2007 | Clayton et al. |
| 7,317,782 | B2 | 1/2008 | Bjorkholm |
| 7,423,273 | B2 | 9/2008 | Clayton et al. |
| 7,636,417 | B2 | 12/2009 | Bjorkholm |
| 8,263,938 | B2 | 9/2012 | Bjorkholm |
| 2002/0071520 | A1 | 6/2002 | Springer et al. |
| 2003/0165211 | A1 | 9/2003 | Grodzins et al. |
| 2003/0190011 | A1 | 10/2003 | Beneke et al. |
| 2004/0068169 | A1 | 4/2004 | Mansfield et al. |
| 2004/0256565 | A1 | 12/2004 | Adams et al. |
| 2004/0258189 | A1 | 12/2004 | Norman et al. |
| 2005/0134203 | A1 | 6/2005 | Salop et al. |
| 2007/0210255 | A1 | 9/2007 | Bjorkholm |
| 2007/0241282 | A1 | 10/2007 | Clayton et al. |

FOREIGN PATENT DOCUMENTS

| | | |
|---|---|---|
| JP | 8-68768 | 3/1996 |
| WO | WO 92/02892 | 2/1992 |
| WO | WO 93/14419 | 7/1993 |
| WO | WO 97/18462 | 5/1997 |
| WO | WO 03/067770 | 8/2003 |
| WO | WO 2005/008586 | 1/2005 |

OTHER PUBLICATIONS

"Performance Specification for the Cargo Advanced Automated Radiography System (CAARS)" U.S. Department of Homeland Security, Domestic Nuclear Detection Office (DNDO), Feb. 3, 2005; Document No. DNDO PS-100150v.12: Fed Biz Opps Federal Business Opportunities website (http://fbo.gov), posted Feb. 17, 2006.

"Performance Specification for the Cargo Advanced Automated Radiography System (CAARS), Attachment 2"; U.S. Department of Homeland Security, Domestic Nuclear Detection Office (DNDO), Feb. 24, 2006; Document No. DNDO PS-100150v2.00; Fed Biz Opps Federal Business Opportunities website (http://fbo.gov), posted Feb. 24, 2006.

"Performance Specification for the Cargo Advanced Automated Radiography System (CAARS), Attachment 2"; U.S. Department of Homeland Security, Domestic Nuclear Detection Office (DNDO), Apr. 19, 2006; Document No. DNDO PS-100150v3.00; Fed Biz Opps Federal Business Opportunities website (http://fbo.gov), posted May 1, 2006.

"Section C—Part 1 Statement of Work for the Development of the Cargo Advanced Automated Radiography System", pp. 1-26, "Part 2 Statement of Work for the Production of the Cargo Advanced Automated Radiography System", pp. 27-50; Fed Biz Opps Federal Business Opportunities website (http://fbo.gov), posted Feb. 17, 2006.

"CAARS RFP HSHQDC-05-R-0007-0005, Attachment 1—Responses to RFP & SOW Questions and Comments"; Fed Biz Opps Federal Business Opportunities website (http://fbo.gov), posted Apr. 3, 2006.

"CAARS RFP HSHQDC-05-R-0007-0005, Attachment 2—Responses to Specification Questions and Comments"; Fed Biz Opps Federal Business Opportunities website (http://fbo.gov), posted Apr. 3, 2006.

"Attachment 1 Section C-Part 1—Statement of Work, Development of the Cargo Advanced Automated Radiography System (CAARS)", pp. 1-26, "Part 2—Statement of Work for the Production of the Cargo Advanced Automated Radiography System", pp. 27-50; Fed Biz Opps Federal Business Opportunities website (http://fbo.gov), posted May 1, 2006.

"Responses to Questions at One on One Sessions"; Fed Biz Opps Federal Business Opportunities website (http://fbo.gov), posted May 1, 2006.

H.W. Hon and J.P.O. Evans; "Multiple-view line-scan imaging"; IEE Proceedings—Optoelectronics, vol. 149, No. 2, pp. 45-50, Apr. 2002.

McDonald, Marci; "Checkpoint Terror Border Searches Snarl the Free Flow of Goods" U.S. News and World Report, p. 52, Feb. 11, 2002.

Moore et al.; "Better Imaging: The Key to Better Cargo Inspection", Port Technology International, 2001, pp. 113-119.

Office Action dated Oct. 31, 2006 from U.S. Appl. No. 11/070,030.
Office Action dated Aug. 1, 2007 from U.S. Appl. No. 11/070,030.
Office Action dated Mar. 25, 2008 from U.S. Appl. No. 11/070,030.
Office Action dated Dec. 10, 2008 from U.S. Appl. No. 11/070,030.
Office Action dated Jun. 23, 2009 from U.S. Appl. No. 11/070,030.
Office Action dated Apr. 15, 2010 from U.S. Appl. No. 11/070,030.
Office Action dated Oct. 25, 2010 from U.S. Appl. No. 11/070,030.
Office Action dated Dec. 2, 2011 from U.S. Appl. No. 11/070,030.
Notice of Allowance dated Jun. 29, 2011 from U.S. Appl. No. 11/070,030.

* cited by examiner

DUAL ANGLE RADIATION SCANNING OF OBJECTS

RELATED APPLICATION

The present application is a division of U.S. patent application Ser. No. 11/485,150, which was filed on Jul. 12, 2006, will issue on Mar. 20, 2012 bearing U.S. Pat. No. 8,137,976, and is incorporated by reference herein.

FIELD OF THE INVENTION

Radiation scanning of objects, including large objects such as cargo containers, to identify contraband.

BACKGROUND OF THE INVENTION

Radiation is commonly used in the non-invasive inspection of contents of objects, such as luggage, bags, briefcases, cargo containers, and the like, at airports, seaports, and public buildings, for example, to identify hidden contraband. The contraband may include hidden guns, knives, explosive devices, illegal drugs, and weapons of mass destruction, such as a nuclear or a "dirty" radioactive bomb, for example. During radiation scanning, an object is irradiated by a radiation beam. Radiation transmitted through the object, which is attenuated to varying degrees by the contents, dependent on the densities of the materials through which the radiation beam passes, is detected. Higher density materials or regions within the object attenuate radiation more than less dense materials, resulting in darker or lighter regions on an X-ray image, depending on how the detected radiation is processed and displayed.

One common inspection system is a line scanner, where the object to be inspected is passed between a stationary source of radiation, such as X-ray radiation, and a stationary detector. The radiation is collimated into a fan beam or a pencil beam. The radiation transmitted through the object is detected and measured. Radiographic images of the contents of the object may be generated for inspection. The images show the shape, size and varying densities of the contents.

Fissionable, fissile, and fertile materials ("nuclear materials") have high atomic numbers (Z) and high densities. Their presence, therefore, causes high attenuation of a radiation beam passing therethrough. Fissile materials, such as uranium-235 (Z=92), uranium-233 (Z=92), and plutonium-239 (Z=94), may undergo fission by the capture of a slow (thermal) neutron. Fissionable materials include fissile materials, and materials that may undergo fission by capture of fast neutrons, such as uranium-238. Fertile materials may be converted into fissile materials by the capture of a slow (thermal) neutron. Uranium-238, for example, may be converted into plutonium-239. Thorium-232 (Z=90), for example, may be converted into uranium-233. Fissionable, fissile, and fertile material are referred to herein as "nuclear material." Special Nuclear Material ("SNMs"), which more readily undergo fission than other fissile materials, are defined by the U.S. Nuclear Regulatory Commission to include plutonium, uranium-233, and uranium enriched in the isotopes of uranium-233 or -235. All of these materials have densities of about 20 g/cm$^3$.

Radioactive materials, certain of which may have lower atomic numbers and densities than nuclear materials (cobalt-60, for example, has an atomic number of 27 and a density of about 9 g/cm$^3$), are typically shielded during shipping by high atomic number materials, such as lead (Z=82) or tungsten (Z=74). Lead has a density of about 11 g/cm$^3$ and tungsten has a density of about 19 g/cm$^3$. These shielding materials also cause high attenuation. Iron, which is a main material in a majority of industrial goods shipped in cargo conveyances, in contrast, which has an atomic number of 26 and a density of about 8 g/cm$^3$, causes less attenuation. Agricultural goods, which may also be shipped in cargo conveyances, have even lower atomic numbers and densities. It is noted, however, that large amounts of even low density materials, such as agricultural goods, along a line of sight of a radiation beam, can also cause high attenuation of radiation.

While the smuggling of guns, explosives and other contraband onto planes in carry-on bags and in luggage has been a well known, ongoing concern, a less publicized but also serious threat is the smuggling of contraband across borders and by boat in large cargo containers. Only 2%-10% of the 17 million cargo containers brought to the United States by boat are inspected. "Checkpoint Terror", U.S. News and World Report, Feb. 11, 2002, p. 52.

Standard cargo containers are typically 20-50 feet long (6.1-15.2 meters), 8 feet high (2.4 meters), and 6-9 feet wide (1.8-2.7 meters). Air cargo containers, which are used to contain a plurality of pieces of luggage or other cargo to be stored in the body of an airplane, may range in size (length, height, width) from about 35×21×21 inches (0.89×0.53×0.53 meters) up to about 240×118×96 inches (6.1×3.0×2.4 meters). Large collections of objects, such as many pieces of luggage, may also be supported on a pallet. Pallets, which may have supporting side walls, may be of comparable sizes as cargo containers and use of the term "cargo conveyance" encompasses cargo containers and pallets.

Atomic bombs and "dirty bombs," which use a conventional explosion to disperse radioactive material over a wide territory, are examples of nuclear devices that may be smuggled in cargo conveyances and smaller objects. Radioactive, fissionable, fissile, and fertile materials that may be used to manufacture atomic devices, may also be similarly smuggled in such objects.

A variety of techniques are being used to locate nuclear devices, nuclear materials, and radioactive materials (that may not be nuclear materials), in cargo conveyances. Manual inspection of the contents of an object is too slow for regular use. Identification of radioactive materials and nuclear devices by passive inspection systems, such as a radiation detector, while faster, is difficult, because the dense materials absorb most of the photons they emit. Shielding material, such as lead or tungsten, may also be used to block the escape of radiation, preventing its detection. In addition, certain fissile materials, such as uranium-233, uranium-235, and plutonium-239 while radioactive, have exceedingly long half-lives (on the order of $10^4$-$10^8$ years). The count rate from spontaneous decays for such material is so low, that passive detection is not reliable. Also, a relatively small amount of radioactive material may be located within a large cargo conveyance. It is also difficult to distinguish nuclear devices and nuclear materials from other dense items that may be contained within the object by standard X-ray scanning at one or multiple radiation energies.

In one example of an X-ray scanning system, U.S. Pat. No. 5,524,133 discloses scanning systems for large objects, such as freight in a container or on a vehicle. In one embodiment, two stationary sources of X-ray radiation are provided, each emitting a beam that is collimated into a fan beam. The sources face adjacent sides of the freight and the fan beams are perpendicular to each other. A stationary detector array is located opposite each source, on opposite sides of the freight, to receive radiation transmitted through the freight. In addition, X-ray radiation of two different energies are emitted by each source. One energy is significantly higher than the other. For example, energies of 1 MeV and 5 or 6 MeV may be used. A ratio of the mean number of X-rays detected at each energy endpoint by the detector array as a whole for each slice or by the individual detectors of the array is determined and compared to a look up table to identify a mean atomic number corresponding to the ratio. The material content of the freight is thereby determined.

One complication with the use of such X-ray scanning devices is that measurements of radiation after interaction with the object under inspection are statistical. The accuracy of a measurement of X-ray radiation transmitted through an object is limited by the number of photons used to make the measurement, as well as intrinsic system noise, for example. Repeated measurements of the same quantity typically yield a cluster of measurement values around a mean value. A plot of the cluster of measurements typically forms a "normal distribution" curve. The dispersion of the individual measurements (the width of the normal distribution curve) is characterized by a standard deviation. Insufficient photons may be detected to enable measurement distributions with small standard deviations. The distributions for materials of interest, such as uranium, may therefore overlap the distributions of other, non-threatening materials. It may not, therefore, be clear whether a particular measurement is indicative of a material of interest or not, resulting in either a high false positive rate or a low sensitivity.

The standard deviation decreases and the accuracy of measurement increases as more photons are detected. While the number of photons detected may be increased by increasing the scanning time, it is generally not acceptable to slow the throughput rate of a typical X-ray scanning system at ports, borders, or airports, for example.

The accuracy of a scanning system seeking to identify a material, such as uranium, for example, may be characterized by its "sensitivity" and its "specificity". Sensitivity is the probability that the presence of uranium in a cargo conveyance will be identified. A system with high sensitivity will identify more true positives (correct identification of the presence of uranium) and fewer false negatives (missed detection of uranium) than a system with low sensitivity. However, increased sensitivity may result in an increase in the number of false positives, which may not be acceptable. Specificity, which is a statistical measure of accuracy, is the probability that the scanning system will properly identify the absence of uranium in a cargo conveyance, for example. A system with high specificity will identify fewer false positives (identification of uranium in a cargo conveyance when it is not present), than a system with low specificity.

In U.S. Pat. No. 6,347,132 B1 ("Annis"), a high energy X-ray inspection system for detecting nuclear weapons materials is described wherein an object is scanned by a high energy X-ray fan beam or pencil beam. A detected signal is processed to identify an area of high X-ray attenuation within the object. Such high attenuation is considered to be indicative of the presence of nuclear materials.

SUMMARY OF THE INVENTION

Since an X-ray image is a two-dimensional representation of a three-dimensional space, it cannot be determined from the detected X-ray signal or from a resulting X-ray image whether a region of high density is due to attenuation caused by a small region of very high density, high atomic number material ("HANM"), along the line of sight of the X-ray radiation, which may be a nuclear material or shielding material for nuclear material, or attenuation caused by a larger region of moderate and/or low density, innocuous material or materials along the line of sight of the X-ray beam. For example, 5 cm of a material having a moderate density of about 8 g/cm$^3$, such as iron, would cause about the same attenuation and would therefore appear to have about the same density in an X-ray image as 2 cm of the HANMs uranium or plutonium, which have densities of about 20 g/cm$^3$. Large regions of moderate and/or low density materials will therefore cause false positives for nuclear/shielding material in X-ray images, that need to be further investigated. This causes unnecessary delays in processing of many cargo conveyances, luggage, etc.

To resolve this ambiguity without having to manually inspect the contents of an object, in embodiments of the present invention, objects may be scanned at least two different angles. In one example, if a high density region is found from scanning the object at the first angle, the object is scanned at a second angle. In this way, the contents of the object contributing to the radiation attenuation resulting in the high density region at the first angle, may be examined at the second angle. If scanning at the second angle also results in a high density region, it is more likely that HANM, which may be nuclear material or shielding material for HANM, is present in the object. If not, then it is not likely that nuclear material is present. The size of the object may optionally be taken into consideration, as well. For example, scanning at the second angle may only take place if a high density region greater than a predetermined size of concern is found at the first angle. Images may be visually examined and/or data underlying the images or the detected radiation itself may be automatically examined.

In accordance with an embodiment of the invention, a method of examining contents of an object is disclosed comprising scanning at least a portion of an object by a first radiation beam at a first angle and detecting radiation interacting with the object at the first angle. The method further comprises scanning at least the portion of an object by a second radiation beam at a second angle different than the first angle and detecting radiation interacting with the object at the second angle. The method further comprises determining whether the object at least potentially contains high atomic number material based, at least in part, on the detected radiation at the first and second angles.

In accordance with another embodiment of the invention, a method of examining contents of an object is disclosed comprising scanning at least a portion of an object by a first X-ray radiation beam generated by a first X-ray source, at a first angle and detecting first radiation transmitted through the object by a first detector. The method further comprises determining whether the object at least potentially contains nuclear material based, at least in part, on the detected radiation. If it is determined that the object at least potentially contains nuclear material, the method further comprises scanning at least the portion of the object by a second X-ray radiation beam generated by a second X-ray source different than the first X-ray source, at a second angle different than the first angle, detecting second radiation transmitted through the object by a second detector, and determining whether the object at least potentially contains nuclear material based, at least in part, on the second detected radiation.

In accordance with another embodiment of the invention, a system for examining contents of an object is disclosed comprising means for scanning at least a portion of an object at first and second, different angles, means for detecting radiation interacting with the object at the first and second angles, and means for determining whether the object at least potentially comprises high atomic number material, based, at least in part, on the radiation detected at the first and second angles.

In accordance with another embodiment of the invention, a system for examining contents of an object is disclosed comprising at least one radiation source to scan at least a portion of an object at first and second, different angles and at least one detector positioned to detect radiation at the first and second angles. The system further comprises at least one processor coupled to the detector. The at least one processor is configured to determine whether the object at least potentially comprises high atomic number material based, at least in part, on the radiation detected at the first and second angles.

DESCRIPTION OF THE PREFERRED EMBODIMENTS

Figure 1:
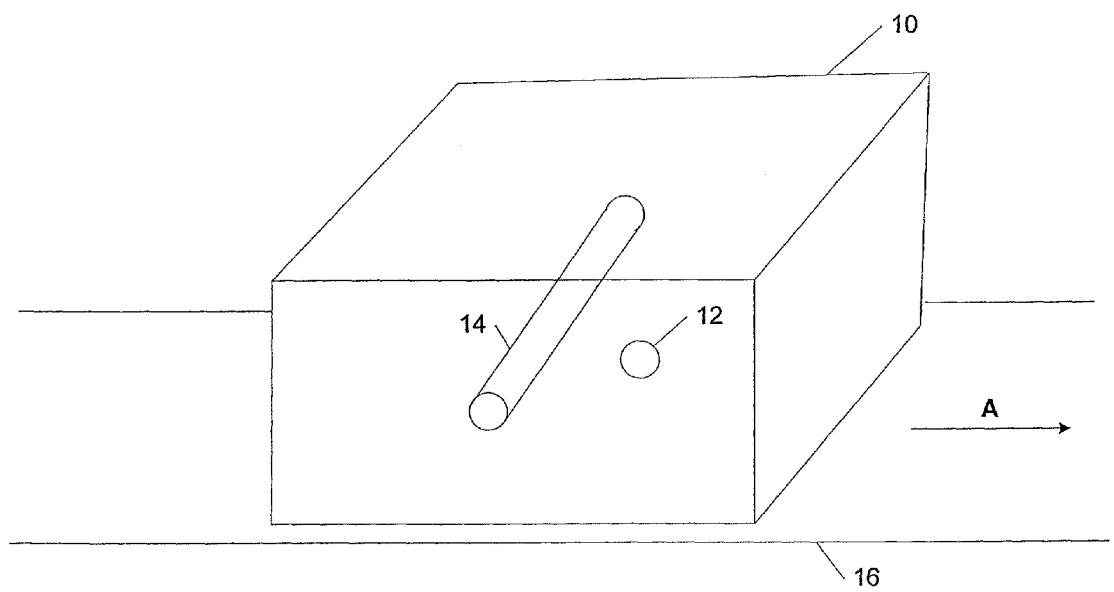
FIG. 1 is a perspective view of an example of an object containing a sphere and a solid pipe, moving through an example of a prior art X-ray scanning system.
Figure 2:
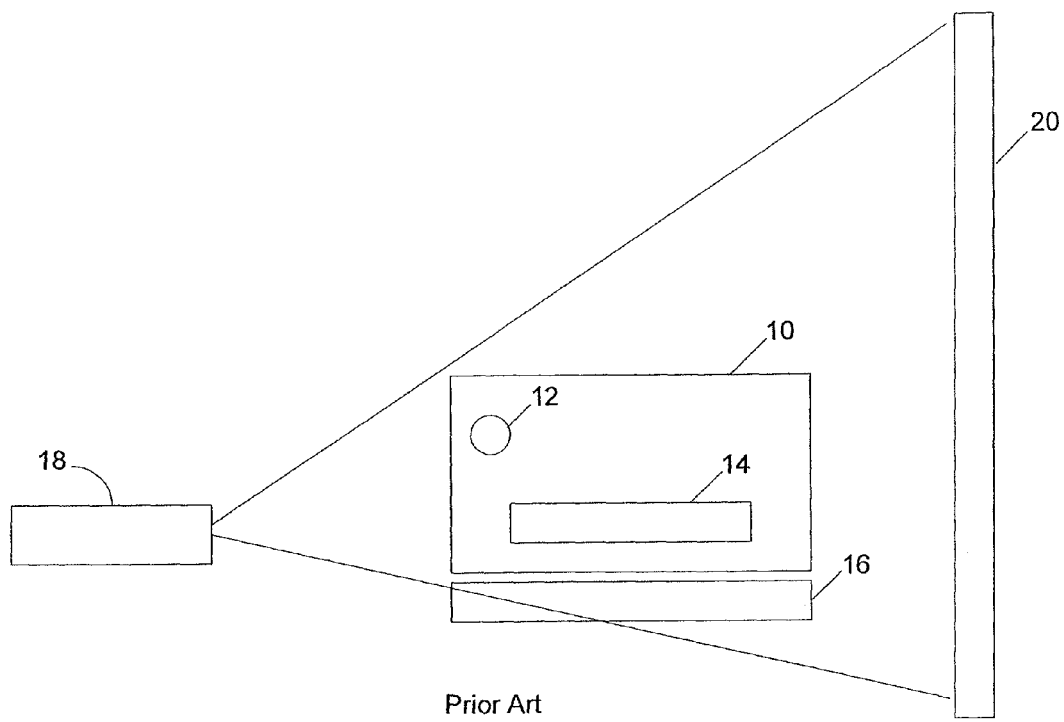
FIG. 2 is a front view of the object moving through the X-ray scanning system of FIG. 1.
Figure 3:
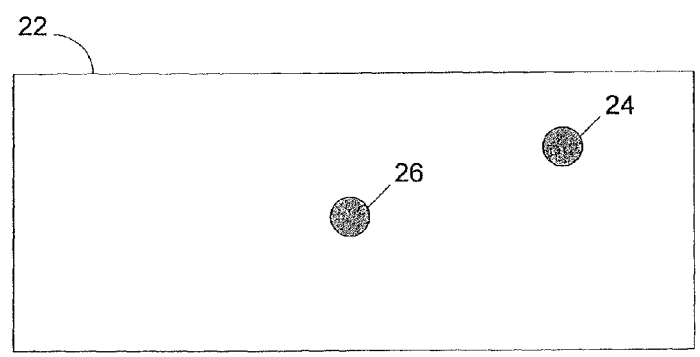
FIG. 3 is an example of an X-ray image resulting from radiation scanning of the object by the X-ray scanning system of FIG. 1.

FIG. 1 is a perspective view of an example of an object 10, such as a rectangular cargo conveyance, containing a sphere 12 of a high density SNM, such as uranium-233 (density of about 20 g/cm$^3$) and a solid pipe 14 of a moderate density material, such as iron (density of about 8 g/cm$^3$), for example, moving through an example of an X-ray scanning system. The object 10 is on a conveyor 16, moving to the right, as indicated by arrow A. FIG. 2 is a front view of the object 10 on the conveyor 16, also showing a radiation source 18 and a detector 20. FIG. 3 is an example of an X-ray image 22 resulting from radiation scanning of the object 10, including the sphere 12 of high density material, indicated by a high density region 24, and the iron pipe 14, indicated by a high density region 26. In this example, the pipe 14 has a length such that the radiation attenuation caused by the pipe is comparable to the attenuation caused by the sphere 12 of uranium. The two regions 24, 26 are therefore indistinguishable in the image 22.

In accordance with embodiments of the invention, objects are examined at least two angles by radiation scanning to identify materials that may be high density, high atomic number materials ("HANMs") within the object. Such HANM may be a nuclear material or shielding for a nuclear material. In one example, if a high density region is identified in a first radiographic image derived from radiation scanning at a first angle, then a second radiographic image derived from radiation scanning of a portion of the object including the high density region at a second angle is examined. If the corresponding portion of the object appears to have high density at the second angle, as well, it is likely that an HANM, which may be a nuclear material or shielding for a nuclear material, is present. If not, then nuclear or shielding material is not likely to be present. The images may be visually analyzed or automatically analyzed by a processor. A processor may analyze the data underlying the image or the detected radiation, instead of or along with visual inspection. The processor may also determine the size of the high density region and take that into consideration. For example, the second image may only be examined if the high density region of the first image is greater than or equal to a predetermined minimum size of concern.

A class of materials to be defined as HANM may be chosen by an operator or supplier of the system, for example. In one example, this is done by selecting an atomic number at or above which materials will be considered HANM. For example, HANM may be defined by the system to include special nuclear materials ("SNMs") by selecting an atomic number at least greater than or equal to the atomic number of uranium (Z=92), for example. HANM may be defined by the system to include SNMs and shielding material by selecting an atomic number at least greater than or equal to the atomic number of lead (Z=74), for example. HANM may be defined by the system to include materials having an atomic number greater than iron, for example by selecting an atomic number of at least 26. In another example, HANM are defined as materials having a density at or above a selected density, such as 10 g/cm$^3$, for example.

Figure 4:
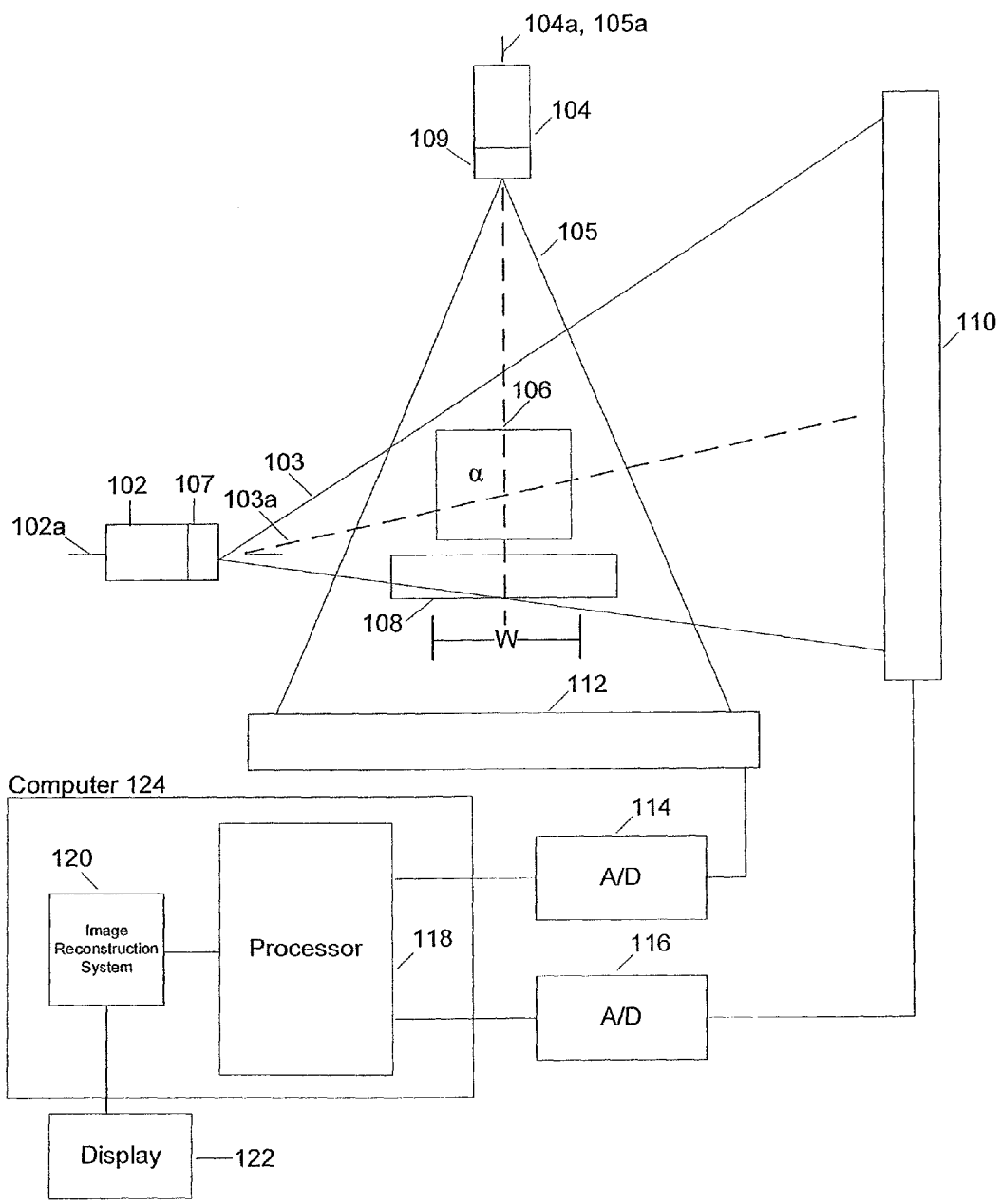
FIG. 4 is a schematic representation of a front view of an example of a radiation scanning system in accordance with an embodiment of the invention.

FIG. 4 is a schematic representation of a front view of an example of a radiation scanning system 100 in accordance with an embodiment of the invention. The system 100 comprises a first radiation source 102 and a second radiation source 104, positioned to irradiate an object 106 on a conveyor 108 at two different angles with first and second radiation beams 103, 105, respectively. A first detector 110 faces the first source 102 and a second detector 112 faces the second source 104, on an opposite side of the object 106. The first and second detectors are coupled to analog-to-digital ("A/D") circuitry 114, 116, respectively, which are coupled to a processor 118. The processor 118 may be coupled to an image reconstruction system 120, which is coupled to a display 122. The processor 118 may also be directly coupled to the display 122. The processor 118 and/or the image reconstruction system 120 may be part of one or more computers 124. Multiple processors 118, image reconstruction systems 120, and computers 124 may be provided. An operator's console (not shown) is also typically provided to directly or indirectly control the operation of the system 100.

Collimators 107, 109 are coupled to the radiation sources 102, 104. The collimators 107, 109 include slots (not shown), to collimate the X-ray radiation into a beam having a desired shape. In one example, the collimators 107, 109 define fan beams. Alternatively, the slots 107, 109 may define a cone beam, such as an asymmetric pyramidal cone beam, or a pencil beam. The collimators 107, 109 may have other shapes, as well. The collimator 107 may define a radiation beam having a different shape than the collimator 109. For example, the slot 107 may define a cone beam and the slot 109 may define a fan beam or a pencil beam. Use of a first, broader cone beam may enable more rapid scanning of the object 106. If a suspect region is found, scanning at the second angle may be performed with a second fan beam or pencil beam. This could reduce the overall radiation exposure of the object 106, as well.

If the radiation sources 102, 104 are linear accelerators, they may be positioned so that their longitudinal axes 102a, 104a, respectively, are substantially perpendicular, as shown in FIG. 4. The central axes 103a, 105a of the radiation beams 103, 105 may or may not be perpendicular to each other, as well. For example, in the example of FIG. 4, since the source 102 is positioned at about the same height as the conveyor 108, the radiation beam 103 is not emitted symmetrically with respect to the longitudinal axis 102a of the source. The central axis 103a of the beam 103 is not, therefore, aligned with the longitudinal axis 102a of the source 102. The central axis 105a of the beam 105, in contrast, is aligned with the central axis 104a of the source.

The central axes 103a, 105a, intersect to form an angle $\alpha$, as shown in FIG. 4. The angle $\alpha$ is an angle that provides sufficient additional information about a suspect high density region identified by scanning at the first angle, to determine whether the high density region is potentially due to HANM. In one example, that additional information is in a second dimension different than the dimension of the first scanning angle, to provide a "perspective" view of the suspect high density region, yielding additional information about the density and size of the suspect region. In one example, the angle $\alpha$ is at least 20° and not greater than 160°. In another example, the angle $\alpha$ is at least 30° and not greater than 150°. In another example, the angle $\alpha$ is at least 45° and not greater than 135°. In another example, the angle $\alpha$ is at least 60° and not greater than 120°. In another example, the angle $\alpha$ is about 90°.

The sources 102, 104 may also be positioned and the radiation beams 103, 105 collimated such that the central axes 103a, 105a lie in the same plane or in different planes, such as parallel planes. If the axes 103a, 105a are different, the first source 102 needs to be upstream of the second source 104 so that a longitudinal location of the object 106 passes the first source 102 before passing the second source 104.

The conveyor 108 supports and conveys the object 106 through the scanning system 100, between the X-ray sources 102, 104 and the detectors 110, 112. The conveyor system 108 may be a mechanically driven conveyor belt, a track or mechanically driven rollers, for example. The conveyor 108 may be transparent to radiation, as is known in the art.

To examine objects 106 having a width "W" greater than about 5 feet (1.5 meters), such as larger cargo conveyances, the X-ray sources 102, 104 may generate radiation having energy endpoints greater than about 1 MeV. 5 MeV or 9 MeV may be used, for example. In examining objects having a width W less than about 5 feet (1.5 meters), the X-ray sources 102, 104 may generate energy in the keV range. For example, 600 keV may be used.

One or both of the radiation sources 102, 104 may be sources of X-ray radiation, such as Bremsstrahlung radiation. For example, the sources 102, 104 may be linear accelerators, such as a Linatron® Linear Accelerator ("Linatron®"), having an accelerating potential at an appropriate level or levels, available from Varian Medical Systems, Inc., Palo Alto, Calif. ("Varian"), for example. In the Varian Linatron®, 360 pulses are output per second. The Varian Linatron® has an opening angle of about 20-30 degrees, for example. The X-ray sources 102, 104 may be other types of sources, such as electrostatic accelerators, microtrons and betatrons, for example. The source or sources 102, 104 may also include carbon-12 (C-12), cobalt-60 (Co-60), plutonium-beryllium (Pu—Be), and/or americium-beryllium (Am—Be) based sources. One or both of the radiation sources 102, 104 may also be a source of neutrons. X-ray tubes may be used as radiation sources 102, 104 in the KeV range.

The first and second detectors 110, 112 collect radiation interacting with the object 106. In the example of FIG. 4, radiation transmitted through the object 106 is detected. Scatter imaging could also be used, in addition to transmission imaging. Scatter imaging could be used instead of or in addition to transmission imaging. Scatter imaging could be used exclusively with smaller objects, such as luggage, for example. The detectors 110, 112, or other detectors, could be suitably positioned to detect scattered radiation, as is known in the art.

The detectors 110, 112 may be in the form of a detector array. The configuration of the detectors 110, 112 may depend on the shape of the respective collimated radiation beams 103, 105. For example, if either or both of the radiation beams 103, 105 are collimated into fan beams, the corresponding detector arrays 110, 112 may comprise one-dimensional detector arrays, comprising a single row of detector elements. If either or both of the collimated radiation beams are cone beams, such as asymmetric pyramidal cone beams, the corresponding detector arrays 110, 112 may comprise two dimensional detector arrays 110, 112 comprising two or more adjacent rows of detector elements. Either or both of the detector arrays 110, 112 may comprise a plurality of modules of detectors, each comprising one or more rows of detector elements supported in a housing, as is known in the art. Either or both of the detectors 110, 112 or detector arrays may be straight, as shown in FIG. 4, or L-shaped, as is known in the art. If either or both of the radiation beams 103, 105 are collimated into pencil beams, a one-dimensional detector may be used.

The detectors 110, 112 may be photon detectors, such as a photodiode detector array comprising inorganic scintillators, as is known in the art. Cadmium tungstate ($CdWO_4$) scintillators may be used, for example. Amorphous silicon (aSi) detectors, such as PaxScan™ detectors available from Varian Medical Systems, Inc., Palo Alto, Calif., may also be used.

The values of the intensities of the radiation transmitted through the object and by the detected detectors 110, 112 are stored as arrays in memory (not shown) of a scanning system for processing by the A/D converters 114, 116 and the computer 124, for example. The size of the pixels may depend on the size and/or number of detector elements comprising the detectors 110, 112, imaging integration time, etc. The smallest pixel size may correspond to a single detector element or number of detector elements. The size of each detector element and each pixel may be 0.5 cm×0.5 cm, for example.

Other X-ray scanning system components known in the art are not shown herein, for ease of illustration. For example, the object 106 may be conveyed through a shielded tunnel with windows to allow for radiation passage from the sources 102, 104 to the object 106 and from the object to the detectors 110, 112. The entire system 100 may be shielded by concrete or a multilayer shield comprising polyethylene as an inner layer and lead or steel as an outer layer, for example. X-ray scanning systems are described in more detail in U.S. application Ser. No. 11/070,030, U.S. application Ser. No. 11/070,143, and U.S. application Ser. No. 11/070,032, all of which were filed on Feb. 28, 2005, are assigned to the assignee of the present invention, and are incorporated by reference herein.

In operation, the object 106 is moved by the conveying system 108 in a direction out of the page in the view of FIG. 4. The object 106 may be moved continuously through the radiation beams 103, 105 or the object may be moved incrementally. As the object 106 is moved, the first and second sources 102, 104 irradiate the object with radiation. Alternatively, the second source 104 may only be activated if a suspect region of high density is found after scanning by the first source 102. The conveyor 108 may be reversed for rescanning.

Figure 5A:
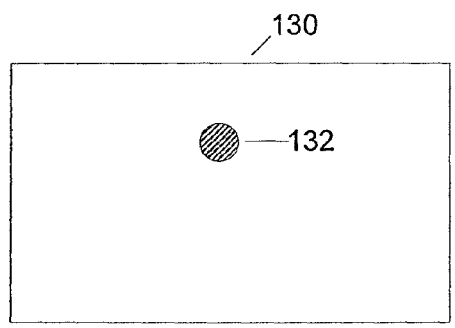
FIG. 5a is an example of an X-ray image of the contents of an object resulting from scanning by the radiation scanning system of FIG. 4, at a first angle.

FIG. 5a is an example of an X-ray image 130 derived from radiation scanning by the first radiation source 102 and collected by the first detector 110, at a first longitudinal location of the object 106. A small, sphere-shaped dense region 132 is shown. As discussed above, such a dense region could result from scanning of a high density HANM, which could be nuclear material, such as SNM. However, the same dense region 132 could be caused by a long solid pipe of moderate or low density material, such as iron, for example.

Figure 5B:
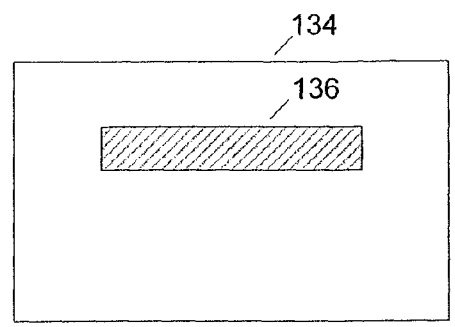
FIG. 5b is an example of an X-ray image of the contents of the object of FIG. 5 at a second angle, where the contents do not include high atomic nuclear material.

To resolve this ambiguity, in this example an image is reconstructed from scanning by the second source 104 and analyzed. FIG. 5b is an example of an X-ray image 134 of the same object 108 at the same first longitudinal location of the object, derived from radiation scanning at a second angle by the second radiation source 104. In this example, the image 134 shows an elongated region 136 of moderate density corresponding to the apparently high density region 132 of FIG. 5a. It can therefore be concluded with a high level of confidence that there is no HANM that may be nuclear material or shielding material, in the object 106. The object 106 can therefore proceed along the stream of commerce.

Figure 5C:
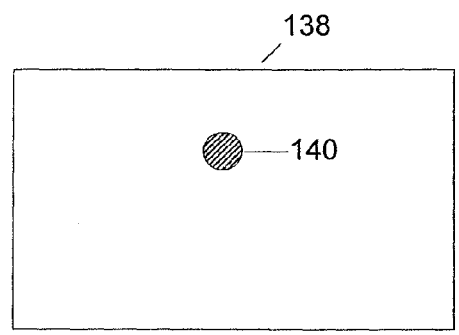
FIG. 5c is another example of an X-ray image of the object of FIG. 5 at the second angle, where the contents include high atomic nuclear material.

In FIG. 5c, which is another example of an X-ray image 138 of the same object 106 at the same first longitudinal location, derived from radiation scanning at a second angle, a sphere shaped high density region 140 of about the same size as the sphere shaped high density region 132 in FIG. 5a, is present. The high density region 132 is not, therefore, due to the projected density along the line of sight of the radiation beam 103 through moderate and/or low density material. In this example, it can be concluded with a higher level of confidence that the high density regions 132, 140 in both images correspond to HANM in the object 108 than if only an image or images at one angle were analyzed. As noted above, that HANM could be nuclear material, such as uranium, or shielding material, such as lead or tungsten, shielding nuclear material. An alarm or other such indicator may be set off automatically or manually, and the object 106 may be moved to a safe place for further inspection and possible disposal of the object and its contents.

The manifest for the object 108 may then be checked to determine whether an innocuous HANM, such as platinum, gold, silver, or molybdenum, for example (depending on the atomic number where HANM is defined to start in a particular system), has been declared. If not, or regardless, the object 108 may then be diverted for further testing, such as manual inspections or other non-invasive examinations, such as other radiation scanning techniques. The high density material in the object 108 and in the image may have other shapes, as well, such as oval, cubic, or rectangular, for example.

As mentioned above, the second source 104 may be activated to generate a radiation beam only if a suspect region is found in an image derived from scanning by the first radiation source 102. In this way, the radiation exposure of the object is not increased unnecessarily. Images may then be derived from scanning by the second radiation source 104 only of the suspect region. Alternatively, scanning may be conducted by the second source 104 continuously and the entire object may be scanned at both angles.

It may be desirable to require that the high density region in an image resulting from scanning by the first source be greater than a minimum size of concern prior to scanning at the second angle or examining an image at the second angle. The minimum size of concern may be a cube with sides of 4.5 cm or a sphere of corresponding volume, for example. In a recent Department of Homeland Security Solicitation for Cargo Advanced Automated Radiography System (CAARS), Solicitation No. HSHQDC-05 R-0007, posted Jan. 10, 2006, available on the Fed Biz Opps Federal Business Opportunities website (http://fbo.gov) at www.fbo.gov/spg/DHS/OCPO/DHS-OCPO/HSHQDC%2DO5%2DR % D0007/listing.html, identification of HANM behind 10 inches (25 mm) of steel having a volume of 100 cubic centimeters, is required. A cube with 4.5 cm walls, for example, has a volume of 91.125 $cm^3$.

The images may be readily reviewed by an operator of a scanning system, who may view images from an operator's console (not shown), on the display 122, for example. High density regions in images resulting from scanning at the first angle can be readily identified visually, based on the contrast of regions of the image. High density regions may appear to be darker or lighter than the surrounding portions of an image, depending on how the detected radiation is processed into the image. Upon identification of such high density regions, the operator may initiate scanning at the second angle of the same longitudinal location as the first image or through the portion of the object corresponding to the high density region in the first image. The results may again be displayed and visually analyzed and compared on the display 122.

The images or the data underlying the images may be automatically analyzed as well, by comparing detected radiation intensities to a function, such as a threshold, for example. The function may be based on a predetermined atomic number or density at or above which it is desired to identify an HANM. In one example, an image density threshold is established, when an X-ray system 100 is calibrated on site. Thresholds may be established for each radiation angle. Threshold generation is discussed further, below.

Images or data from scanning at one angle may then be automatically analyzed to identify regions with intensities indicative of densities that meet or exceed the density threshold. Regions that do not exceed the threshold do not have atomic numbers and densities high enough to potentially correspond to nuclear materials or shielding materials and in this example are not of concern.

If only nuclear materials and shielding materials greater than a certain size are of concern, a size threshold may also be created. The size of the high density region may be automatically determined by counting contiguous pixels having intensities greater than the threshold, discussed above, for example. High density regions may be automatically identified by comparing the intensity of image pixels or groupings of pixels to the predetermined threshold based on the calibration discussed above, as is known in the art.

As discussed above, in one example, HANMs are defined as materials having an atomic number greater than a predetermined atomic number. The predetermined atomic number may be determined based on the materials that it is desired to identify. For example, uranium (Z=92) has the lowest atomic number of the SNMs. To be sure to identify at least potential SNMs, the predetermined atomic number may be 92 or less. To also be able to identify the presence of the shielding materials lead (Z=82) and tungsten (Z=74), the predetermined atomic number may be 74 or less. Since radiation attenuation/transmission is related to the density of the materials along the path of the radiation through the object, density may be used to define a function, such as a threshold, to differentiate HANM from non-HANM based on the detected radiation. HANM may be defined in terms of density as well.

Figure 6:
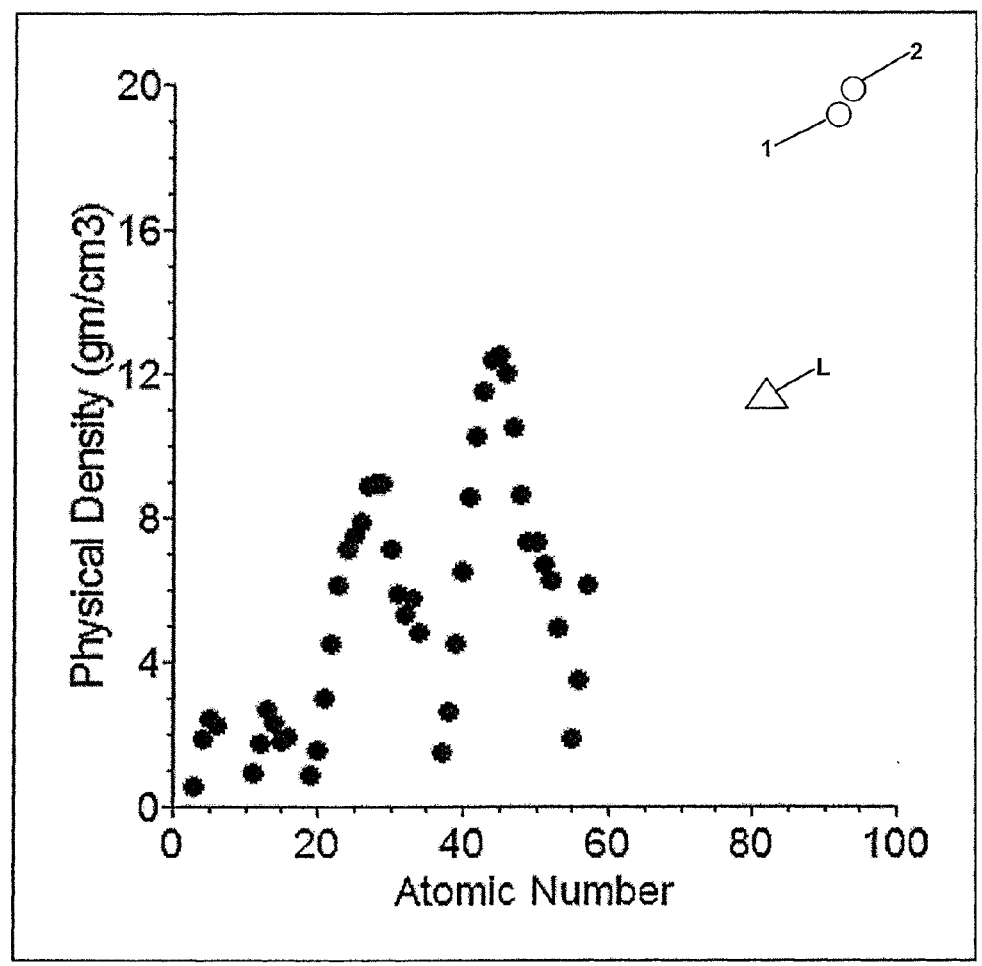
FIG. 6 is a graph of Physical Density (g/cm$^3$) versus Atomic Number for metals up to an atomic number of 57 (indicated by black points) and certain other elements.

FIG. 6 is a graph of Physical Density ($g/cm^3$) versus Atomic Number for metals up to an atomic number of 57 (indicated by black points) and certain other elements. The physical density of lead (atomic number 82) of about 11 $g/cm^3$ is indicated by an open triangle "L". The physical densities of uranium and plutonium are indicated by Circle 1 and Circle 2, respectively. Uranium has a density of about 19.5 $g/cm^3$ and plutonium has a density of about 19.7 $g/cm^3$. The physical densities of uranium and plutonium are nearly twice that of lead and the other metals.

Lead (Z=82) has the lowest density of materials of interest in this example. To provide sufficient margin to be sure to identify lead, a density threshold may be based on a density of 10 $g/cm^3$. However, as shown in FIG. 6, molybdenum (atomic number 42, density 10.2 $g/cm^3$), rhodium (atomic number 45, density 12.4 $g/cm^3$), palladium (atomic number 46, density 12.0 $g/cm^3$), and silver (atomic number 47, density 10.5 $g/cm^3$) have comparable densities. Of these metals, only silver is shipped in significant amounts and when it is, it is typically identified on a manifest. Therefore, in actual commerce, the presence of high density, non-nuclear, non-shielding materials should not cause many nuisance alarms. Other thresholds may be selected as well.

The material densities in FIG. 6 are three dimensional values having units of $g/cm^3$, for example. When scanning at each angle, however, the detected radiation at each angle is only indicative of the radiation transmitted through or attenuated by an "effective," "projected," or "line of sight" density, which is a two dimensional value having units of $g/cm^2$, for example. For this reason, the radiation detected after passing through a small amount of uranium and a large amount of iron along the line of sight of the radiation beam, may be the same, as may the resulting radiation images. Without being limited to any theory of operation, embodiments of the invention scan at a second angle to obtain information about the material contents of the container along the line of sight of the radiation beam at the first angle, in the third dimension.

In one example, a threshold corresponding to 10 $g/cm^3$, discussed above with respect to FIG. 6 (or any other selected density), may be determined by calculating the effective density of a material having a density of 10 $g/cm^3$, along a line of sight of the smallest HANM of concern. For example, if it is desired to identify HANM of a cube having sides of 4.5 cm or a sphere having a diameter of 4.5 cm, for example, the threshold may be calculated by multiplying the actual material density (10 $g/cm^3$) by the length or diameter of the object of concern (4.5 cm), which yields a two dimensional projected density threshold of 45 $g/cm^2$.

The scanning system 100 may be calibrated to the desired two dimensional projected density threshold by scanning a cube of a material having the same effective density as the threshold at one or both scanning angles. A cube having sides of 45 cm, for example, which has a density of 1 $g/cm^3$, has an effective density of 45 g/cm. Cube sizes of other materials, such as aluminum and steel, may be readily calculated, as well. The detected radiation and/or the image densities in resulting images may then be used as thresholds.

According to the Department of Homeland Security Solicitation for Cargo Advanced Automated Radiography System (CAARS), Solicitation No. HSHQDC-05 R-0007, posted Jan. 10, 2006 identified further, above, a radiation scanning system should identify a material with an atomic number greater than 72 as a HANM. Those specifications also require that materials having an atomic number less than 57 not be considered HANM. Hafnium, which has an atomic number of 72, has a density of about 13.2 $g/cm^3$. A threshold to identify HANM above an atomic number of 72 having a size of a 4.5 cm cube, or other size, may be readily defined based on the density of hafnium, for example, as described above. The density of tantalum (Z=73), which has a density of 16.6 $g/cm^3$, could be used, as well.

As discussed above, materials with an atomic number between 56 and 72 are rarely transported in commerce and when they are, they are typically declared on a manifest. High atomic number, high density limits defining HANM as materials with atomic numbers greater than 72, for example, will include as HANM nuclear materials and shielding materials. Most commonly shipped metals, such as tin (Z=50), silver (Z=47), molybdenum (Z=42), zinc (Z=30), copper (Z=29), nickel (Z=28), cobalt (Z=27), and iron (Z=26) would not be identified as HANM. It is noted that cobalt (Z=27) and carbon (Z=6) have radioactive isotopes (cobalt-60, carbon-12), which would not be identified as an HANM if the predetermined atomic number is greater than 27. However, since radioactive materials would probably be transported within lead or tungsten shielding material, its presence could be identified by detecting the presence of the high atomic number shielding material.

Since iron (Z=26) is the highest atomic number material commonly found in cargo conveyances and luggage, the threshold detection may be based on iron. To avoid nuisance alarms caused by the presence of iron, in this example, HANM could be defined as materials having an atomic number greater than 26. Copper (Z=29) and nickel (Z=28), which have atomic numbers close to iron, could also be used in a similar way.

The threshold may also be established by scanning a piece of test material having a predetermined atomic number or density, in the scanning system 100 at each angle, detecting the radiation interacting with the piece, and processing the detected radiation. If HANM are defined in a particular system to be materials having an atomic number greater than iron (Z=26), for example, a piece of iron could be used. The test material may be in a shape of a cube having a size of the smallest SNM of concern. For example, the test piece may be a cube having sides of 4.5 cm. The function may be the same or may be different for the two scanning angles, depending on the state and position of the system components, such as the sources 102, 104 and the detectors 110, 112.

Figure 7:
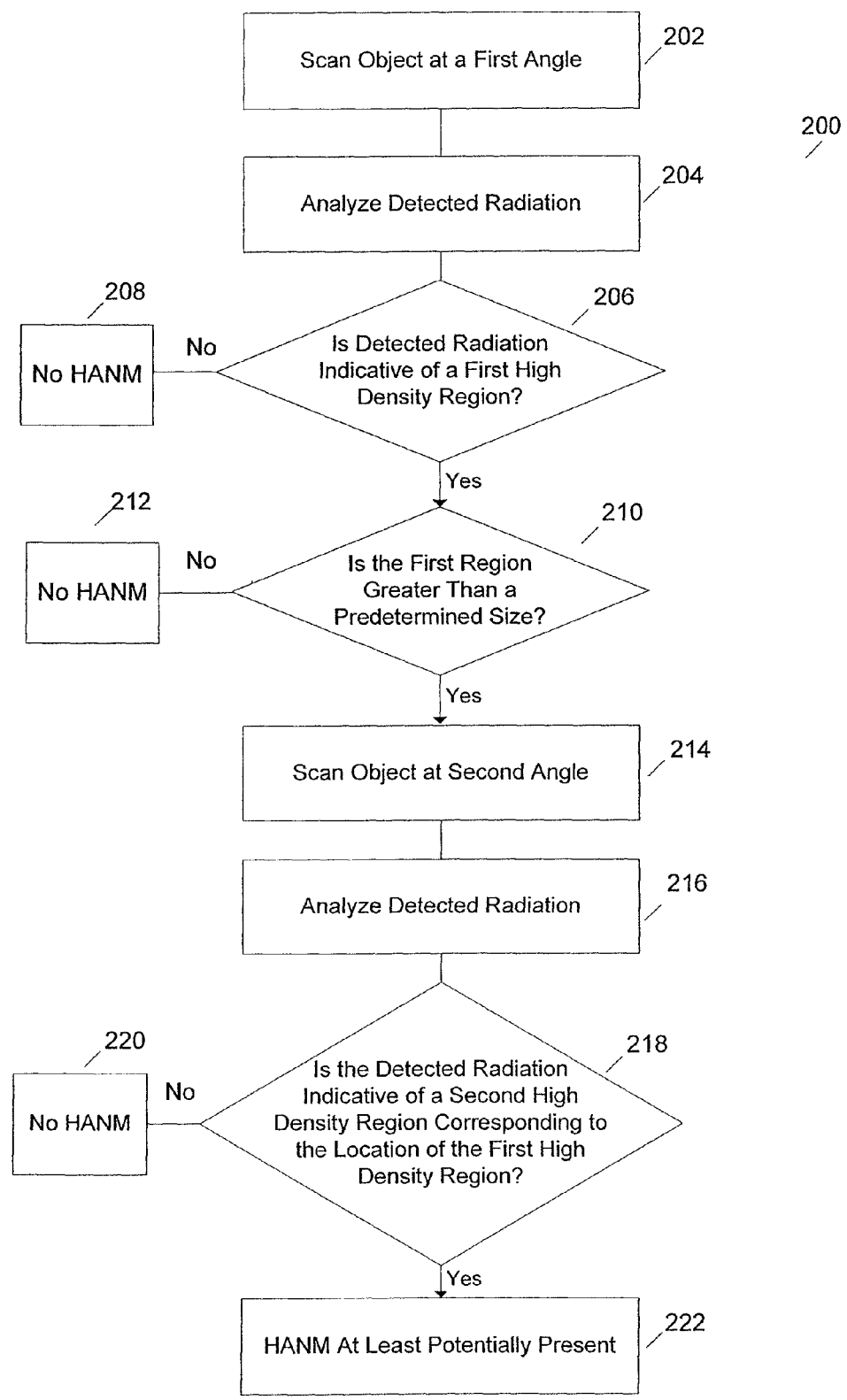
FIG. 7 is an example of a method for examining objects in accordance with an embodiment of the invention.

FIG. 7 is an example of a method 200 for examining objects in accordance with an embodiment of the invention. An object is scanned at a first angle, in Step 202. Detected radiation is analyzed, in Step 204. It is then determined whether the detected radiation is indicative of the presence of a first high density region in the object, in Step 206. This may be determined automatically by a processor 118, such as the computer 124, configured to analyze an image or data underlying the image by comparison to a density threshold, for example. If not, it is determined that there is no HANM present, in Step 208.

If the detected data is indicative of a high density region in the object, in this example it is determined whether the size of the region is greater than a predetermined size, in Step 210. This may also be determined automatically by the processor 118, such as the computer 124, by comparison to a diameter or area threshold. If not, then it is concluded that high density HANM is not present, in Step 212.

If the high density region is greater than the predetermined size, in this example, at least a portion of the object at the same longitudinal location of the object corresponding to the first high density region, is scanned at the second angle, in Step 214. The detected radiation is analyzed, in Step 216, and it is determined whether the detected data is indicative of a second high density region corresponding to the location of the first high density region in the object, in Step 218. As above, this may be done automatically.

If the detected data is not indicative of a second high density region corresponding to the location of the first high density region in the object, then it is determined that an HANM is not present, in Step 220.

If the detected data is indicative of a second high density region corresponding to the location of the first high density region, then it is concluded that HANM is at least potentially present, in Step 222. A visual or audible alarm may be automatically initiated by the processor 118/computer 124, if HANM is found. The manifest may then be checked to determine whether non-nuclear HANM, such as silver (Z=47), in this example, has been declared. This may also be done automatically by the processor/computer, if an electronic manifest is provided, or by an operator. If not, or regardless, the object may be removed from the conveyor 108 for further testing, such as manual inspection and/or additional radiation scanning, as discussed further below.

The processor 118/computer 124 may be programmed in software and/or hardware to automatically analyze the images and/or data, and to control operation of the system 100. In one example, the methods of embodiments of the invention may be implemented through an Application Specific Integrated Circuit (ASIC), for example.

Steps 206 and 218 may also be performed visually by an operator viewing images of the object. If visual inspection of images is conducted, the size check in step 210 may optionally be skipped.

Figure 8:
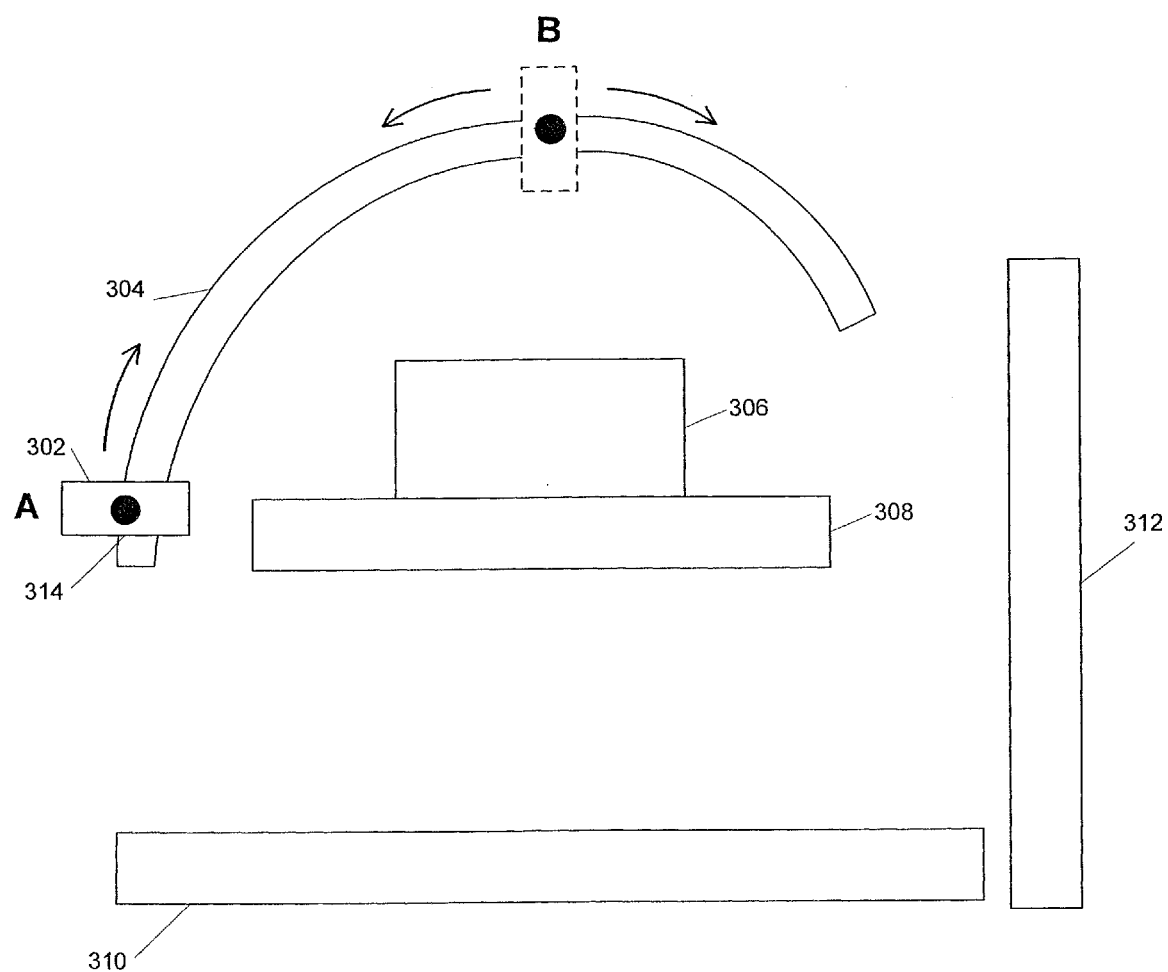
FIG. 8 is a schematic representation of another example of a radiation scanning system in accordance with an embodiment, in which a radiation source is movably supported on a rail.

FIG. 8 is a schematic representation of another example of a radiation scanning system 300 in accordance with another embodiment, in which a radiation source 302 is movably supported on a rail 304. An object 306 is shown supported by a conveyor 308 that moves the object out of the page in this view. The source 302 is shown in a first position A for scanning at a first angle. The source 302 is movable to a second position, such as position B (shown in phantom), for scanning at a second angle. Other components of the system 300, such as those shown in FIG. 4 and discussed above, as well as others known in the art, are not shown in this view to ease illustration.

The source 302 may be moved along the rail 304 by chains (not shown) driven by a motor (not shown), for example. Two detectors 310, 312 are also shown. The source 302 may be coupled to the rail via a hinge 314 so that the source may be rotated into a desired alignment with the object 306 in the different positions A, B.

The rail 304 is arcuate, such as semi-circular, in this example, but it may have other configurations. For example, it may be straight. The rail 304 may extend somewhat more than one-quarter circle, to enable scanning at positions up to about 90° apart, or to somewhat more than about 135°, for example.

If a suspect region is found by scanning in the first position A, the operator can cause the source 302 to be moved to the second position B and initiate scanning. A processor, such as the computer 124, may be programmed to automatically identify potential HANM based on detected radiation, as discussed above, and may also be programmed to automatically advance the source 302 to the second position B and initiate scanning.

In one example, the positions A and B are predetermined and the source 302 is only movable between those positions. The second position B may be any position enabling scanning at a second angle forming an angle α with the first beam in the ranges discussed above.

In another example, the source 302 is movable from a first to one or a plurality of second predetermined positions along the rail, or may be moved to any desired position between positions A and B. In this example, an operator may determine the second angle to scan an object. If the image or data collected at the second angle is not sufficient to determine whether the object is likely to contain HANM, the source 302 may be moved to another position.

Figure 9:
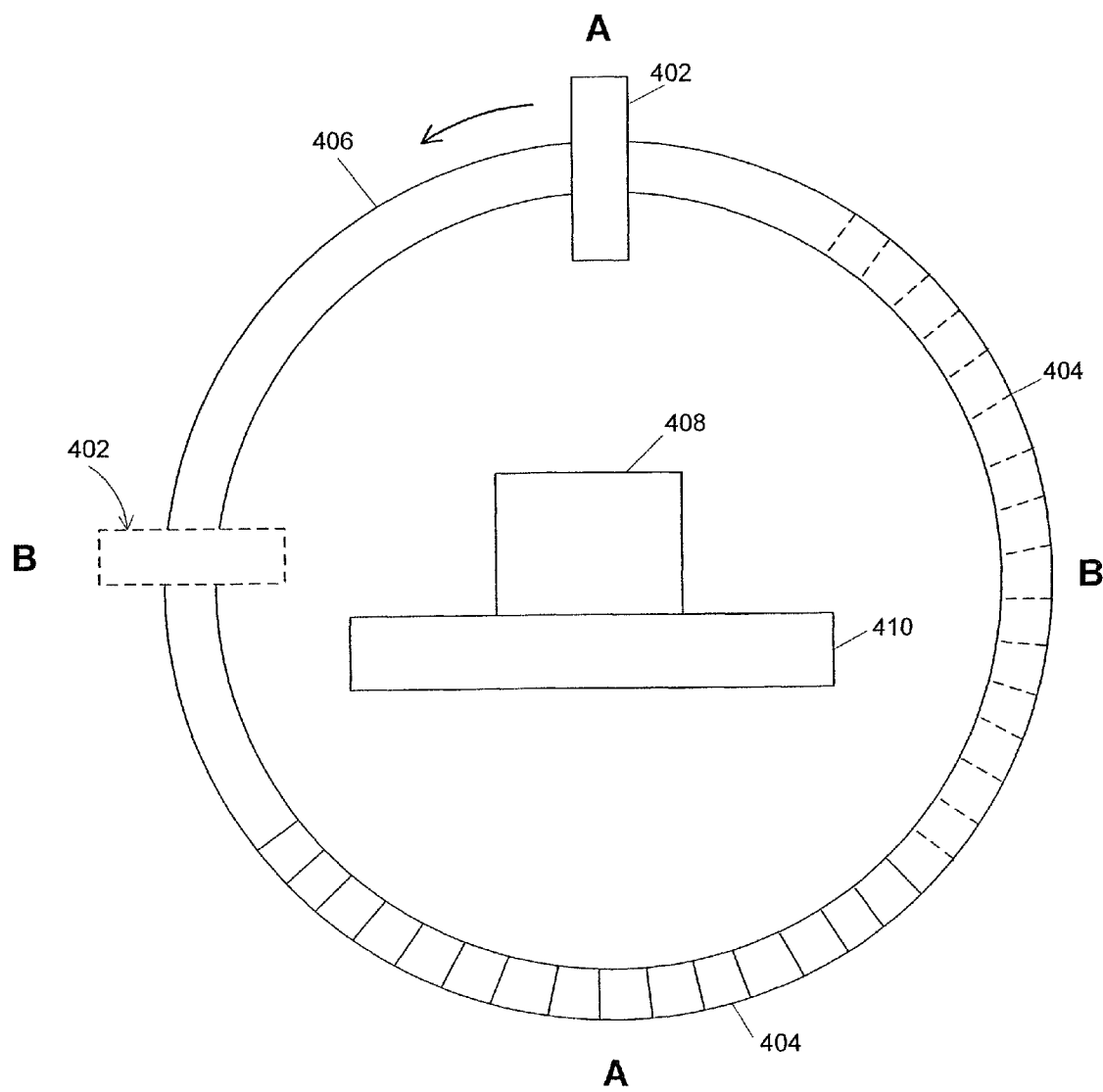
FIG. 9 is a schematic representation of another example of a radiation scanning system in accordance with an embodiment of the invention, wherein a radiation source and a detector are movably supported on a gantry.

A radiation source 402 and a detector 404 may also be movably supported on a circular gantry 406, as shown in FIG. 9. An object 408 supported by a conveyor 410 that moves the object out of the page in this view, are also shown. The gantry 406 may be rotatable clockwise or counterclockwise, here counterclockwise, to position the source 402 and the detector 404 in a first position A and a second B (shown in phantom). As above, the positions A and B may be determined or may be set by an operator. The gantry 406 may move the source 402 and the detector 404 to different and/or additional positions. Other components of the system 400, such as those shown in FIG. 4 and discussed above, as well as others known in the art, are not shown in this view to ease illustration. The source 402 and the detector 404 may also be supported by a C-arm connected to a rotating gantry. Such a C-arm type scanning system is described in U.S. Patent Publication No. US 2004/0068169 A1, which was published on Apr. 8, 2004, is assigned to the assignee of the present invention, and is incorporated by reference herein.

Figure 10:
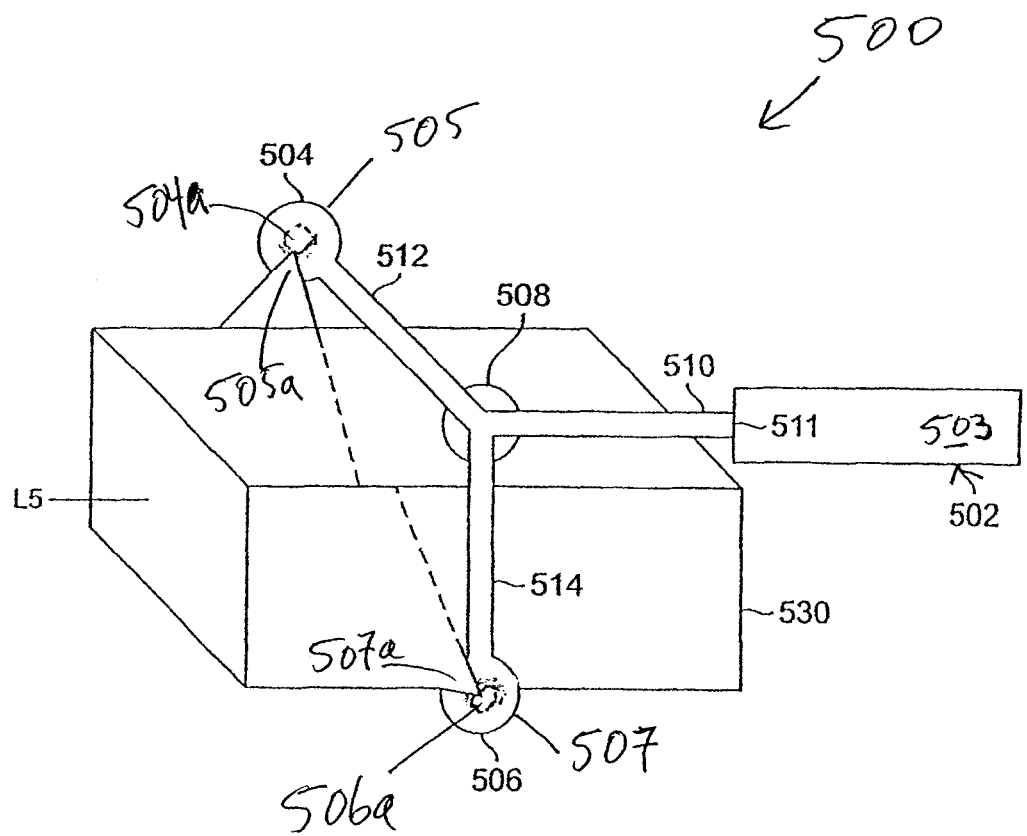
FIG. 10 is a schematic representation of another example of a radiation scanning system in accordance with an embodiment of the invention, in which a radiation source comprises two targets, to generate radiation to irradiate an object at two angles.

FIG. 10 is a schematic representation of another example of a radiation scanning system 500 in accordance with another embodiment of the invention, in which a radiation source 502 comprises a source of charged particles (not shown) coupled to an accelerator body 503 and two shielded targets 504, 506 to generate radiation to irradiate an object 530 at two angles. The object is moved to the left, as indicated by the arrow L, by a conveyor (not shown). The detectors are also not shown in this view, to ease illustration. Other components of the system 500, such as those shown in FIG. 4 and discussed above, as well as others known in the art, are not shown in this view to ease illustration.

The shielded targets 504, 506 comprise target material 504a, 506a (shown in phantom) surrounded by shielding material 505, 507. The shielding material 505, 507, which may be tungsten, for example, defines slots 505a, 507a, respectively, extending from the targets 504a, 506a to the exterior of the shielding material, to define a radiation beam at a desired angle and having a desired shape, directed towards the object 530. A fan beam or a cone beam may be defined, for example. Such a shielded target is described in more detail in U.S. application Ser. No. 10/199,781, which was filed on Jul. 19, 2002, was published on Mar. 25, 2004 as U.S. Publication No. 20040057554 A1, is assigned to the assignee of the present invention, and is incorporated by reference herein.

An electron beam from the linear accelerator body 503 is selectively directed to one of the two shielded targets 504, 506 by an electromagnetic bend magnet 508. A first drift tube 510 extends from the output end 511 of the linear accelerator body 502 to the bend magnet 508. Two drift tubes 512, 514 extend at right angles from the bend magnet 508, to the two shielded targets 504, 506.

The two shielded targets 504, 506 are positioned to irradiate the object 530 at two different angles. The targets 504, 506 may irradiate the object 530 at two different longitudinal positions. The detectors (not shown) may be straight or L-shaped detectors, as above. In operation, the electromagnetic bend magnet 508, which is a well known device, is used to deflect the electron beam into one or the other tube 512, 514 as the object 530 is conveyed through the scanning unit. In accordance with an embodiment of the present invention, the magnet 508 may deflect the election beam towards the shielded target 506 for scanning at a first angle, and if a suspected HANM is identified, the magnet 508 may be automatically or manually switched to deflect the electron beam towards the shielded target 504 for scanning at a second angle, as described above. Alternatively, the magnet 508 may be automatically switched to alternately deflect the electron beam to the first and second shielded targets 504, 506, as the object 530 is conveyed through the system 500.

Figure 11:
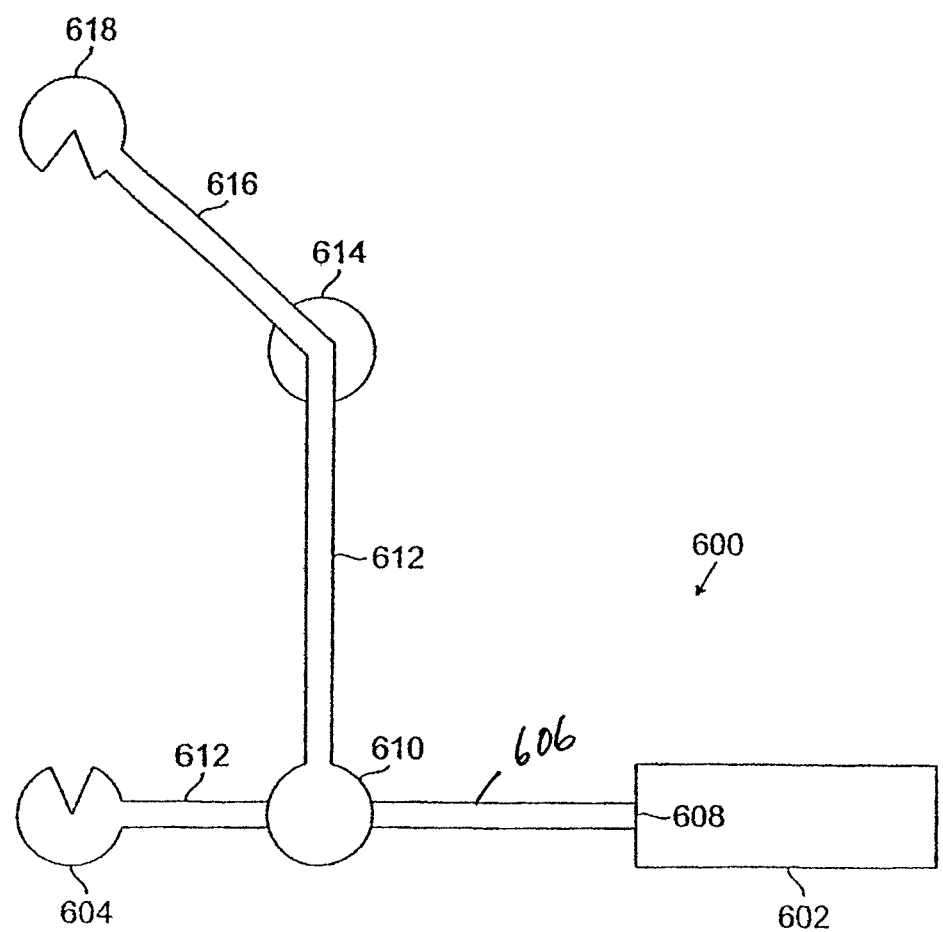
FIG. 11 is a perspective view of an example of a radiation source similar to that in FIG. 10, comprising a linear accelerator body aligned with one of two targets.

Depending on space constraints in the configuration of the scanning unit, it may be advantageous to align the linear accelerator body 502 with one of the shielded targets. FIG. 11 is a perspective view of an X-ray source 600, comprising a linear accelerator body 602 that is aligned with a first shielded target 604. A first drift tube 606 couples the open end 608 of the linear accelerator body 602 to a first bend magnet 610. A second drift tube 612 couples the first bend magnet 610 to the first shielded target 604. A third drift tube 612 couples the first bend magnet 610 to a second bend magnet 614. A fourth drift tube 616 couples the second bend magnet 614 to a second shielded target 618. The first bend magnet 614 selectively allows the electron beam to pass to the first shielded target 604 or deflects the electron beam to the second shielded target 618. The first bend magnet 604 is an electromagnet. In this case, the second bend magnet 614, which may always be on, may be a permanent magnet or an electromagnet.

The method and system of the present invention may be combined with other examination methods and systems. For example, a first examination of the container may be conducted by a dual energy technique. The second radiation source 104 may be at a different energy than the first radiation source 102, a third radiation source (not shown) may be provided to generate radiation at a different energy, or the first or second radiation source 102, 104 may be switched between energy levels. Dual energy techniques are discussed in U.S. application Ser. No. 11/070,030, U.S. application Ser. No. 11/070,143, and U.S. application Ser. No. 11/070,032, all of which were filed on Feb. 28, 2005, are assigned to the assignee of the present invention, and are incorporated by reference herein ("the Dual Energy Applications"). Dual energy techniques are also discussed in U.S. Pat. No. 5,524,133, which is discussed above and is incorporated by reference herein. If a suspected HANM is found by the dual energy technique, then the suspected HANM may be analyzed at the first and second angles. False alarms may thereby be further reduced, without reducing sensitivity.

Alternatively, the dual view technique discussed herein may be a first test. If potential HANM is found, the dual energy tests discussed in the Varian Applications, above, may be conducted to determine whether the potential HANM is an HANM, with a higher level of confidence. Another confirmatory test described in the Dual Energy Applications involves the detection of delayed neutrons, which are indicative of the presence of nuclear material, to verify the dual energy, or other tests. The delayed neutron test may also be used with the dual view test described herein, with or without the dual energy tests described in the Varian Applications.

Since the dual angle test is simpler than many others tests, it may be performed first.

While the invention is particularly suited for scanning cargo conveyances for HANM, the invention may be readily adapted to scan other objects, such as luggage and carry-on bags in airports and seaports, as well.

While in the embodiments described above, the object is moved by a conveyor system through radiation beams generated by radiation sources that are stationary during scanning, the object could be stationary and the radiation sources could be moved across the length of the object. In addition, an object could be moved through the radiation beams by a crane or other such device. For example, the object could be scanned while being moved horizontally or vertically through radiation beams generated by sources mounted on or near the crane. The crane may be loading or unloading cargo containers between a ship and a truck, for example, as described in U.S. application Ser. No. 10/356,101, which was filed on Jan. 31, 2003 and was published as U.S. Publication No. 20040156477 A1 on Aug. 12, 2004, and U.S. application Ser. No. 11/203,491, which was filed on Aug. 12, 2005, and was published as 20060115043 A1 on Jun. 1, 2006, both of which are assigned to the assignee of the present invention and are incorporated by reference herein.

In addition, while an X-ray source or sources are described in the examples above, the source or sources may provide other types of radiation, such gamma rays, for example.

One of ordinary skill in the art will recognize that other changes may be made to the embodiments described herein without departing from the spirit and scope of the invention, which is defined by the claims, below.

What is claimed is:

1. A method of examining contents of an object, comprising:
    scanning at least a portion of an object by a first radiation beam at a first angle;
    detecting radiation interacting with the object at the first angle;
    determining whether the object at least potentially contains high atomic number material having an atomic number greater than a predetermined atomic number based, at least in part, on the radiation detected at the first angle;
    scanning at least the portion of an object by a second radiation beam at a second angle different than the first angle;
    detecting radiation interacting with the object at the second angle; and
    determining whether the object at least potentially contains high atomic number material having an atomic number greater than a predetermined atomic number based, at least in part, on the radiation detected at the second angle; and
    determining that the object at least potentially contains high atomic number material if the determinations at the first and second angles both indicate the at least potential presence of high atomic number material at corresponding longitudinal locations of the object.

2. The method of claim 1, further comprising:
generating first and second images based, at least in part, on the radiation detected at the first and second angles; and
visually determining whether the object at least potentially contains high atomic number material based, at least in part, on the first and second images.

3. The method of claim 1, comprising:
detecting radiation transmitted through the object at the first angle; and
detecting radiation transmitted through the object at the second angle.

4. The method of claim 1, comprising:
scanning at least the portion of the object with first and second radiation beams with respective central axes forming an angle of from about 20° to about 160°.

5. The method of claim 1, comprising scanning the at least a portion of the object with first and second X-ray radiation beams from a single radiation source.

6. The method of claim 1, comprising:
generating the first radiation beam by a first radiation source; and
generating the second radiation beam by a second radiation source different than the first radiation source.

7. The method of claim 1, comprising:
determining that the object does not contain high atomic number material if the radiation detected at only one angle indicates the presence of high atomic number material.

8. The method of claim 1, comprising determining whether the object at least potentially contains high atomic number material by:
comparing the detected radiation at the first angle to a first function based, at least in part, on a predetermined density; and
comparing the detected radiation at the second angle to a second function based, at least in part, on the predetermined density.

9. The method of claim 8, comprising determining whether the object at least potentially contains high atomic number material by:
identifying a region of potential high atomic number material based, at least in part, on the comparing of the detected radiation at the first angle to the first function; and
comparing a size of the identified region of potential high atomic number material to a third function based, at least in part, on a predetermined size.

10. The method of claim 8, comprising:
comparing the detected radiation at the first angle to a first function based, at least in part, on a density of at least 10 g/cm$^3$; and
comparing the detected radiation at the second angle to a second function based, at least in part, on the density of at least 10 g/cm$^3$.

11. The method of claim 8, comprising:
determining whether the object at least potentially contains high atomic number material having an atomic number of at least 57, based, at least in part, on the detected radiation at the first and second angles.

12. The method of claim 1, comprising:
scanning at the first angle by a radiation source at a first position;
moving the radiation source to a second position; and
scanning at the second angle by the radiation source in the second position.

13. The method of claim 1, comprising:
determining that the object at least potentially comprises high atomic number material, based, at least in part, on the radiation detected at only the first and second angles.

14. A method of examining contents of an object, comprising:
scanning at least a portion of an object by a first radiation beam at a first angle;
detecting radiation interacting with the object at the first angle;
determining whether the object at least potentially contains high atomic number material based, at least in part, on the detected radiation at the first angle; and
scanning at least the portion of the object by a second radiation beam at a second angle different than the first angle, only if it is determined that the object at least potentially contains high atomic number material based, at least in part, on the radiation detected at the first angle;
if scanning is conducted at the second angle, detecting radiation interacting with the object at the second angle;
determining whether the object at least potentially contains high atomic number material having an atomic number greater than a predetermined atomic number based, at least in part, on the radiation detected at the second angle; and
determining that the object at least potentially contains high atomic number material if the radiation detected at the first and second angles both indicate the at least potential presence of high atomic number material at corresponding longitudinal locations of the object.

15. A system for examining contents of an object, the system comprising:
at least one radiation source to scan at least a portion of an object at first and second different angles:
at least one detector positioned to detect radiation at the first and second angles; and
at least one processor coupled to the detector, the at least one processor being configured to:
determine whether the object at least potentially contains high atomic number material having an atomic number greater than a predetermined atomic number based, at least in part, on the radiation detected at the first angle;
determine whether the object at least potentially contains high atomic number material having an atomic number greater than a predetermined atomic number based, at least in part, on the radiation detected at the second angle; and
determine that the object at least potentially contains high atomic number material if the first and second determinations at the first and second angles both indicate the at least potential presence of high atomic number material at corresponding longitudinal locations of the object.

16. The system of claim 15, comprising:
a first radiation source positioned to scan the object at a first angle;
a second radiation source positioned to scan the object at the second angle;
a first detector positioned to detect radiation transmitted through the object at the first angle; and
a second detector positioned to detect radiation transmitted through the object at the second angle.

17. The system of claim 15, wherein:
the at least one radiation source is a single radiation source movable between a first position to scan the object at the first angle and a second position to scan the object at the second angle.

18. The system of claim 17, wherein:
the single radiation source is movably supported on a rail or a rotating gantry.

19. The system of claim 18, wherein:
the single radiation source is supported by a rotating gantry; and
the at least one detector comprises a detector supported by the rotating gantry, opposite the source.

20. The system of claim 15, wherein the at least one radiation source comprises:
a source of charged particles;
a first target to generate the first radiation beam;
a second target to generate the second radiation beam; and
at least one magnet to selectively direct the charged particles to the first target or the second target.

21. The system of claim 15, wherein the processor is configured to determine whether the object at least potentially contains high atomic material by:
comparing the radiation detected at the first angle to a first function based, at least in part, on a predetermined density; and
comparing the radiation detected at the second angle to a second function based, at least in part, on the predetermined density.

22. The system of claim 21, wherein the processor is configured to determine whether the object at least potentially contains high atomic number material by:
identifying a region of potential high atomic number material based, at least in part, on the comparing of the detected radiation at the first angle to the first function; and
comparing a size of the region of potential high atomic number material to a third function based, at least in part, on a predetermined size.

23. The system of claim 22, wherein the processor is configured to compare the detected radiation at the first angle to the first function by:
comparing the detected radiation at the first angle to a first function based, at least in part, on a density of at least 10 g/cm$^3$; and
comparing the detected radiation at the second angle to a second function based, at least in part, on the density of at least 10 g/cm$^3$.

24. The system of claim 21, wherein the processor is configured to determine whether the object at least potentially contains high atomic number material by:
comparing the radiation detected at the first angle to the function; and
if the comparison indicates that high atomic number material is at least potentially present:
cause scanning of the object at the second angle; and then
compare the radiation detected at the second angle to the function.

25. The system of claim 21, wherein the processor is configured to:
determine that the object at least potentially contains high atomic number material only if the second comparison indicates that high atomic number material is at least potentially present.

26. The system of claim 15, wherein the processor is configured to:
identify a region of potential high atomic number material based, at least in part, on radiation detected at the first angle;
determine a size of the region of potential high atomic number material;
compare the size to a second function based, at least in part, on a predetermined size; and
if the comparison indicates that high atomic number material is at least potentially present:
cause scanning of the object at the second angle.

27. The system of claim 15, wherein the processor is configured to determine whether the object at least potentially contains high atomic number material by:
determining whether the object at least potentially contains material having an atomic number greater than or equal to a predetermined atomic number based, at least in part, on the radiation detected at the first and second angles.

28. The method of claim 8, wherein the first function defines a first threshold based, at least in part, on a predetermined density, and the second function defines a second threshold based, at least in part, on the predetermined density, the method comprising:
comparing the detected radiation at the first angle to the first threshold, and
comparing the detected radiation at the second angle to the second threshold.

29. The method of claim 1, comprising:
scanning the at least a portion of the object at a plurality of first longitudinal locations at the first angle; and
scanning the at least a portion of the object at a plurality of second longitudinal locations at the second angle.

30. The system of claim 22, wherein the first function defines a first threshold based, at least in part, on a predetermined density and the second function defines a second threshold based, at least in part, on the predetermined density, the method comprising:
comparing the detected radiation at the first angle to the first angle to the first threshold; and
comparing the radiation detected at the second angle to the second threshold.

31. The system of 15, further comprising:
a conveyor to move the object through the system;
wherein the system is configured to:
scan the at least a portion of the object at a plurality of first longitudinal locations at the first angle; and
scan the at least a portion of the object at a plurality of second longitudinal locations at the second angle.

* * * * *